United States Patent
Babaev (10) Patent No.: US 8,235,919 B2
(45) Date of Patent: *Aug. 7, 2012

(54) ULTRASONIC METHOD AND DEVICE FOR WOUND TREATMENT

(75) Inventor: Eilaz Babaev, Minnetonka, MN (US)

(73) Assignee: Celleration, Inc., Eden Prairie, MN (US)

( * ) Notice: Subject to any disclaimer, the term of this patent is extended or adjusted under 35 U.S.C. 154(b) by 504 days.

This patent is subject to a terminal disclaimer.

(21) Appl. No.: 10/409,272

(22) Filed: Apr. 7, 2003

(65) Prior Publication Data

US 2003/0236560 A1    Dec. 25, 2003

Related U.S. Application Data

(63) Continuation-in-part of application No. 09/669,312, filed on Sep. 25, 2000, now Pat. No. 6,569,099.

(51) Int. Cl.
*A61H 1/00* (2006.01)
*A61H 1/02* (2006.01)
*A61H 5/00* (2006.01)

(52) U.S. Cl. .......................................................... 601/2

(58) Field of Classification Search ................... 600/489, 600/437, 439; 601/2–4
See application file for complete search history.

(56) References Cited

U.S. PATENT DOCUMENTS

| | | |
|---|---|---|
| 2,534,046 A | 12/1950 | Mau |
| 2,889,852 A | 6/1959 | Dunlap |
| 3,207,181 A | 9/1965 | Willis |
| 3,243,122 A | 3/1966 | Snaper |
| 3,275,059 A | 9/1966 | McCullough |
| 3,392,916 A | 7/1968 | Engstrom et al. |
| 3,433,226 A | 3/1969 | Boyd |
| 3,504,887 A | 4/1970 | Okerblom |
| 3,522,801 A | 8/1970 | Robinson |
| 3,561,444 A | 2/1971 | Boucher |
| 3,636,947 A | 1/1972 | Balamuth |
| 3,685,634 A | 8/1972 | Bergling |
| 3,685,694 A | 8/1972 | Ianelli |
| 3,765,606 A | 10/1973 | Moss et al. |
| 3,860,173 A | 1/1975 | Sata |
| 3,874,372 A | 4/1975 | Le Bon |
| 3,952,918 A | 4/1976 | Poitras et al. |

(Continued)

FOREIGN PATENT DOCUMENTS

CA       2421798       3/2002

(Continued)

OTHER PUBLICATIONS

"Comparison Possibilities of Ultrasound and Its Combination with Laser in Surgery and Therapy", Zharov et al, pp. 331-339, In Biomedical Optoacoustics.

(Continued)

*Primary Examiner* — Jacqueline Cheng
(74) *Attorney, Agent, or Firm* — Patterson Thuente Christensen Pedersen, P.A.

(57) ABSTRACT

An apparatus and method are provided for generating ultrasonic energy from a non-contact distance from the surface of the wound; and delivering the generated ultrasonic energy to the wound through a gaseous medium. The generated ultrasonic energy has a significantly large amplitude such that the ultrasonic energy has an intensity capable of penetrating the wound tissue to a beneficial depth to provide a therapeutic effect for decreasing the healing time for the wound.

25 Claims, 6 Drawing Sheets

U.S. PATENT DOCUMENTS

| | | |
|---|---|---|
| 4,052,004 A | 10/1977 | Martin et al. |
| 4,085,893 A | 4/1978 | Durley, III |
| 4,153,201 A | 5/1979 | Berger et al. |
| 4,185,502 A | 1/1980 | Frank |
| 4,192,294 A * | 3/1980 | Vasilevsky et al. ............ 606/128 |
| 4,251,031 A | 2/1981 | Martin et al. |
| 4,271,705 A | 6/1981 | Crostack |
| 4,294,407 A | 10/1981 | Reichl et al. |
| 4,301,093 A | 11/1981 | Eck |
| 4,301,968 A | 11/1981 | Berger et al. |
| 4,309,989 A | 1/1982 | Fahim |
| 4,319,155 A | 3/1982 | Nakai et al. |
| 4,331,137 A | 5/1982 | Sarui |
| 4,334,531 A | 6/1982 | Reichl et al. |
| 4,352,459 A | 10/1982 | Berger et al. |
| 4,414,202 A | 11/1983 | Silvetti |
| 4,428,531 A | 1/1984 | Martin |
| 4,466,571 A | 8/1984 | Muhlbauer |
| 4,530,360 A | 7/1985 | Duarte |
| 4,541,564 A | 9/1985 | Berger et al. |
| 4,551,139 A | 11/1985 | Plaas et al. |
| 4,582,149 A | 4/1986 | Slaughter, Jr. |
| 4,582,654 A | 4/1986 | Karnicky et al. |
| 4,619,400 A | 10/1986 | Van Der Burgt |
| 4,642,581 A | 2/1987 | Erickson |
| 4,655,393 A | 4/1987 | Berger |
| 4,659,014 A | 4/1987 | Soth et al. |
| 4,679,551 A | 7/1987 | Anthony |
| 4,726,523 A | 2/1988 | Kokubo et al. |
| 4,726,525 A | 2/1988 | Yonekawa et al. |
| 4,733,820 A | 3/1988 | Endo et al. |
| 4,756,478 A | 7/1988 | Endo et al. |
| 4,767,402 A | 8/1988 | Kost et al. |
| 4,783,003 A | 11/1988 | Hirabayashi et al. |
| 4,790,479 A | 12/1988 | Matsumoto et al. |
| 4,793,339 A | 12/1988 | Matsumoto et al. |
| 4,815,661 A | 3/1989 | Anthony |
| 4,818,697 A | 4/1989 | Liboff et al. |
| 4,850,534 A | 7/1989 | Takahashi et al. |
| 4,877,989 A | 10/1989 | Drews et al. |
| 4,883,045 A * | 11/1989 | Theisz ............................... 601/3 |
| 4,905,671 A | 3/1990 | Senge et al. |
| 4,930,700 A | 6/1990 | McKown |
| 4,941,614 A | 7/1990 | Ilott |
| 4,941,618 A | 7/1990 | Hildebrand et al. |
| 4,961,885 A | 10/1990 | Avrahami et al. |
| 4,982,730 A | 1/1991 | Lewis, Jr. |
| 5,002,059 A | 3/1991 | Crowley et al. |
| 5,013,241 A | 5/1991 | von Gutfeld et al. |
| 5,040,537 A | 8/1991 | Katakura |
| 5,045,066 A | 9/1991 | Scheuble et al. |
| 5,062,795 A | 11/1991 | Woog |
| 5,063,922 A | 11/1991 | Hakkinen |
| 5,067,655 A | 11/1991 | Farago et al. |
| 5,076,266 A | 12/1991 | Babaev |
| 5,104,042 A | 4/1992 | McKown |
| 5,115,805 A | 5/1992 | Bommannan et al. |
| 5,134,993 A | 8/1992 | van der Linden et al. |
| 5,143,588 A | 9/1992 | Liboff et al. |
| 5,152,289 A | 10/1992 | Viebach et al. |
| 5,163,433 A | 11/1992 | Kagawa et al. |
| 5,171,215 A | 12/1992 | Flanagan |
| 5,172,692 A | 12/1992 | Kulow et al. |
| 5,186,162 A | 2/1993 | Talish et al. |
| 5,197,946 A | 3/1993 | Tachibana |
| 5,211,160 A | 5/1993 | Talish et al. |
| 5,219,401 A * | 6/1993 | Cathignol et al. ............ 600/439 |
| 5,231,975 A | 8/1993 | Bommannan et al. |
| 5,259,384 A | 11/1993 | Kaufman et al. |
| 5,269,291 A | 12/1993 | Carter |
| 5,309,898 A | 5/1994 | Kaufman et al. |
| 5,314,441 A | 5/1994 | Cusack et al. |
| 5,315,998 A | 5/1994 | Tachibana et al. |
| 5,316,000 A | 5/1994 | Chapelon et al. |
| 5,318,014 A | 6/1994 | Carter |
| 5,323,769 A | 6/1994 | Bommannan et al. |
| 5,324,255 A | 6/1994 | Passafaro et al. |
| 5,345,940 A | 9/1994 | Seward et al. |
| 5,347,998 A | 9/1994 | Hodson et al. |
| 5,362,309 A | 11/1994 | Carter |
| 5,374,266 A | 12/1994 | Kataoka et al. |
| 5,380,411 A | 1/1995 | Schlief |
| 5,386,940 A | 2/1995 | Berfield |
| 5,393,296 A | 2/1995 | Rattner |
| 5,431,663 A | 7/1995 | Carter |
| 5,437,606 A | 8/1995 | Tsukamoto |
| 5,456,258 A | 10/1995 | Kondo et al. |
| 5,515,841 A | 5/1996 | Robertson et al. |
| 5,515,842 A | 5/1996 | Ramseyer et al. |
| 5,516,043 A | 5/1996 | Manna et al. |
| 5,520,166 A | 5/1996 | Ritson et al. |
| 5,520,612 A | 5/1996 | Winder et al. |
| 5,523,058 A | 6/1996 | Umermura et al. |
| 5,527,350 A | 6/1996 | Grove et al. |
| 5,529,572 A | 6/1996 | Spector |
| 5,545,124 A | 8/1996 | Krause et al. |
| 5,547,459 A * | 8/1996 | Kaufman et al. .................. 601/2 |
| 5,551,416 A | 9/1996 | Stimpson et al. |
| 5,554,172 A | 9/1996 | Horner et al. |
| 5,556,372 A | 9/1996 | Talish et al. |
| 5,573,497 A | 11/1996 | Chapelon |
| 5,611,993 A | 3/1997 | Babaev |
| 5,616,140 A | 4/1997 | Prescott |
| 5,618,275 A * | 4/1997 | Bock ............................ 604/290 |
| 5,626,554 A | 5/1997 | Ryaby et al. |
| 5,630,828 A | 5/1997 | Mawhirt et al. |
| 5,643,179 A | 7/1997 | Fujimoto |
| 5,656,016 A | 8/1997 | Ogden |
| 5,658,323 A | 8/1997 | Miller |
| 5,664,570 A | 9/1997 | Bishop |
| 5,688,224 A | 11/1997 | Forkey et al. |
| 5,699,805 A | 12/1997 | Seward et al. |
| 5,702,360 A | 12/1997 | Dieras et al. |
| 5,707,402 A | 1/1998 | Heim |
| 5,707,403 A | 1/1998 | Grove et al. |
| 5,725,494 A * | 3/1998 | Brisken .......................... 604/22 |
| 5,730,705 A | 3/1998 | Talish et al. |
| 5,735,811 A | 4/1998 | Brisken |
| 5,743,863 A | 4/1998 | Chapelon |
| 5,752,924 A | 5/1998 | Kaufman et al. |
| 5,762,616 A | 6/1998 | Talish |
| 5,785,972 A | 7/1998 | Tyler |
| 5,807,285 A | 9/1998 | Vaitekunas et al. |
| 5,835,678 A | 11/1998 | Li et al. |
| 5,843,139 A | 12/1998 | Goedeke et al. |
| 5,875,976 A | 3/1999 | Nelson et al. |
| 5,879,314 A | 3/1999 | Peterson et al. |
| 5,879,364 A | 3/1999 | Bromfield et al. |
| 5,882,302 A | 3/1999 | Driscoll, Jr. et al. |
| 5,894,841 A | 4/1999 | Voges |
| 5,895,362 A | 4/1999 | Elstrom et al. |
| 5,904,659 A | 5/1999 | Duarte et al. |
| 5,947,921 A | 9/1999 | Johnson et al. |
| 5,957,882 A | 9/1999 | Nita et al. |
| 5,960,792 A | 10/1999 | Lloyd et al. |
| 5,964,223 A | 10/1999 | Baran |
| 5,989,245 A | 11/1999 | Prescott |
| 6,001,069 A | 12/1999 | Tachibana et al. |
| 6,007,499 A | 12/1999 | Martin et al. |
| 6,014,970 A | 1/2000 | Ivri et al. |
| 6,024,718 A | 2/2000 | Chen et al. |
| 6,026,808 A | 2/2000 | Armer et al. |
| 6,027,495 A | 2/2000 | Miller |
| 6,036,661 A | 3/2000 | Schwarze et al. |
| 6,041,253 A | 3/2000 | Kost et al. |
| 6,061,597 A | 5/2000 | Rieman et al. |
| 6,076,519 A | 6/2000 | Johnson |
| 6,083,159 A | 7/2000 | Driscoll, Jr. et al. |
| 6,095,141 A | 8/2000 | Armer et al. |
| 6,098,620 A | 8/2000 | Lloyd et al. |
| 6,102,298 A | 8/2000 | Bush et al. |
| 6,104,952 A | 8/2000 | Tu et al. |
| 6,106,547 A | 8/2000 | Huei-Jung |
| 6,113,558 A | 9/2000 | Rosenschein et al. |
| 6,113,570 A | 9/2000 | Siegel et al. |
| RE36,939 E | 10/2000 | Tachibana et al. |
| 6,139,320 A | 10/2000 | Hahn |

| | | |
|---|---|---|
| 6,158,388 A | 12/2000 | Wenstrand |
| 6,158,431 A | 12/2000 | Poole |
| 6,161,536 A | 12/2000 | Redmon et al. |
| 6,176,839 B1 | 1/2001 | DeLuis et al. |
| 6,186,963 B1 | 2/2001 | Schwarze et al. |
| 6,190,315 B1 * | 2/2001 | Kost et al. ............ 600/309 |
| 6,190,336 B1 | 2/2001 | Duarte et al. |
| 6,206,842 B1 | 3/2001 | Tu et al. |
| 6,206,843 B1 | 3/2001 | Iger et al. |
| 6,231,528 B1 | 5/2001 | Kaufman et al. |
| 6,234,990 B1 | 5/2001 | Rowe et al. |
| 6,251,099 B1 | 6/2001 | Kollias et al. |
| 6,254,294 B1 | 7/2001 | Muhar |
| 6,273,864 B1 * | 8/2001 | Duarte et al. ............ 601/2 |
| 6,296,630 B1 | 10/2001 | Altman et al. |
| 6,311,573 B1 * | 11/2001 | Bhardwaj ............ 73/866.5 |
| 6,314,318 B1 | 11/2001 | Petty |
| 6,321,109 B2 | 11/2001 | Ben-Haim et al. |
| 6,322,527 B1 | 11/2001 | Talish |
| 6,325,769 B1 | 12/2001 | Klopotek |
| 6,392,327 B1 | 5/2002 | Lewis et al. |
| 6,450,417 B1 | 9/2002 | Gipson et al. |
| 6,458,109 B1 | 10/2002 | Henley et al. |
| 6,478,754 B1 * | 11/2002 | Babaev ............ 601/2 |
| 6,500,133 B2 * | 12/2002 | Martin et al. ............ 601/3 |
| 6,533,484 B1 | 3/2003 | Osei et al. |
| 6,533,803 B2 | 3/2003 | Babaev |
| 6,559,365 B2 | 5/2003 | Wilfer |
| 6,569,099 B1 * | 5/2003 | Babaev ............ 600/439 |
| 6,583,071 B1 | 6/2003 | Weidman et al. |
| 6,601,581 B1 | 8/2003 | Babaev |
| 6,623,444 B2 | 9/2003 | Babaev |
| 6,659,365 B2 | 12/2003 | Gipson et al. |
| 6,663,554 B2 * | 12/2003 | Babaev ............ 600/2 |
| 6,666,431 B2 | 12/2003 | McCusker |
| 6,723,064 B2 | 4/2004 | Babaev |
| 6,732,744 B2 | 5/2004 | Olshavsky et al. |
| 6,761,729 B2 | 7/2004 | Babaev |
| 6,772,967 B1 | 8/2004 | Bontems |
| 6,830,556 B2 | 12/2004 | Harmon et al. |
| 6,916,296 B2 | 7/2005 | Soring et al. |
| 6,960,173 B2 | 11/2005 | Babaev |
| 6,964,647 B1 | 11/2005 | Babaev |
| 7,025,735 B2 | 4/2006 | Soring et al. |
| 7,316,664 B2 | 1/2008 | Kadziauskas et al. |
| 7,431,704 B2 | 10/2008 | Babaev |
| 7,572,268 B2 | 8/2009 | Babaev |
| 7,662,177 B2 | 2/2010 | Babaev |
| 7,713,218 B2 | 5/2010 | Babaev et al. |
| 7,729,779 B2 | 6/2010 | Babaev |
| 7,753,285 B2 | 7/2010 | Babaev |
| 7,780,095 B2 | 8/2010 | Babaev |
| 7,785,277 B2 | 8/2010 | Babaev et al. |
| 7,785,278 B2 | 8/2010 | Babaev |
| 7,830,070 B2 | 11/2010 | Babaev |
| 7,914,470 B2 | 3/2011 | Babaev |
| 2002/0062093 A1 | 5/2002 | Soring et al. |
| 2002/0080206 A1 | 6/2002 | Lin |
| 2002/0138036 A1 | 9/2002 | Babaev |
| 2002/0150539 A1 | 10/2002 | Unger |
| 2002/0156400 A1 | 10/2002 | Babaev |
| 2002/0177846 A1 | 11/2002 | Mulier et al. |
| 2003/0023193 A1 | 1/2003 | Soring et al. |
| 2003/0125660 A1 | 7/2003 | Moutafis et al. |
| 2003/0144627 A1 | 7/2003 | Woehr et al. |
| 2003/0153961 A1 | 8/2003 | Babaev |
| 2003/0171701 A1 | 9/2003 | Babaev |
| 2003/0195644 A1 | 10/2003 | Borders et al. |
| 2003/0216687 A1 | 11/2003 | Hwang |
| 2003/0236560 A1 | 12/2003 | Babaev |
| 2004/0015105 A1 | 1/2004 | Ito et al. |
| 2004/0028552 A1 * | 2/2004 | Bhardwaj et al. ............ 422/20 |
| 2004/0030254 A1 | 2/2004 | Babaev |
| 2004/0034982 A1 | 2/2004 | Wieber et al. |
| 2004/0055376 A1 | 3/2004 | Thompson et al. |
| 2004/0068297 A1 | 4/2004 | Palti |
| 2004/0073175 A1 | 4/2004 | Jacobsen et al. |
| 2004/0076175 A1 | 4/2004 | Patenaude |
| 2004/0091541 A1 | 5/2004 | Unger |
| 2004/0186384 A1 | 9/2004 | Babaev |
| 2005/0075587 A1 | 4/2005 | Vago |
| 2005/0075620 A1 * | 4/2005 | Iger ............ 604/500 |
| 2006/0025716 A1 | 2/2006 | Babaev |
| 2006/0058710 A1 | 3/2006 | Babaev |
| 2007/0016110 A1 | 1/2007 | Babaev et al. |
| 2007/0088245 A1 | 4/2007 | Babaev et al. |
| 2007/0090205 A1 | 4/2007 | Kunze et al. |
| 2007/0299369 A1 | 12/2007 | Babaev |
| 2008/0051693 A1 | 2/2008 | Babaev |
| 2008/0132888 A1 | 6/2008 | Iida et al. |
| 2008/0177221 A1 | 7/2008 | Millerd et al. |
| 2008/0183109 A1 | 7/2008 | Babaev |
| 2008/0183200 A1 | 7/2008 | Babaev |
| 2008/0214965 A1 | 9/2008 | Peterson et al. |
| 2008/0243047 A1 | 10/2008 | Babaev |
| 2008/0243048 A1 | 10/2008 | Babaev |
| 2008/0306501 A1 | 12/2008 | Babaev |
| 2009/0018491 A1 | 1/2009 | Babaev |
| 2009/0018492 A1 | 1/2009 | Babaev |
| 2009/0024076 A1 | 1/2009 | Babaev |
| 2009/0043248 A1 | 2/2009 | Peterson |
| 2009/0177122 A1 | 7/2009 | Peterson |
| 2009/0177123 A1 | 7/2009 | Peterson |
| 2009/0187136 A1 | 7/2009 | Babaev |
| 2009/0200394 A1 | 8/2009 | Babaev |
| 2009/0200396 A1 | 8/2009 | Babaev |
| 2009/0222037 A1 | 9/2009 | Babaev |
| 2009/0254005 A1 | 10/2009 | Babaev |
| 2010/0022919 A1 | 1/2010 | Peterson |
| 2010/0076349 A1 | 3/2010 | Babaev |

FOREIGN PATENT DOCUMENTS

| | | |
|---|---|---|
| CA | 2436812 | 8/2002 |
| CN | 1466445 | 1/2004 |
| EP | 0 020 844 | 10/1985 |
| EP | 0416106 | 3/1991 |
| EP | 0 437 155 B1 | 2/1995 |
| EP | 0 657 226 B1 | 2/1998 |
| EP | 0 619 104 | 3/2002 |
| EP | 1 564 009 A2 | 8/2005 |
| GB | 2 099 710 A | 12/1982 |
| GB | 2 101 500 A | 1/1983 |
| JP | 3-73168 | 3/1991 |
| JP | 417844 | 1/1992 |
| JP | 9135908 A | 5/1997 |
| JP | 2000-237275 | 9/2000 |
| RU | 878268 | 11/1981 |
| SU | 910157 B * | 3/1982 |
| SU | 1106485 | 10/1982 |
| SU | 1106485 A | 10/1982 |
| SU | 1176968 A1 | 9/1985 |
| SU | 1237261 A2 | 6/1986 |
| SU | 1827239 | 5/1990 |
| SU | 1704847 A2 | 1/1992 |
| WO | WO 94/06380 | 3/1994 |
| WO | WO 96/35383 | 11/1996 |
| WO | 97/17933 | 5/1997 |
| WO | 02/24150 A2 | 3/2002 |
| WO | WO02/24150 | 3/2002 |
| WO | WO 02/28350 A2 | 4/2002 |
| WO | 02/055131 A2 | 7/2002 |
| WO | 02/060525 A2 | 8/2002 |
| WO | WO02/060525 | 8/2002 |
| WO | WO02/095675 | 11/2002 |
| WO | WO 2007/002598 | 1/2007 |

OTHER PUBLICATIONS

European Search Report dated Sep. 13, 2004.
International Search Report dated Oct. 1, 2004.
XP-002294548, Abstract corresponding to SU 914099.
90/007,613, Sep. 25, 2000, Babaev.
U.S. Appl. No. 90/007,613, filed Sep. 25, 2000, Babaev.
Iraniha, S., et al. "Determination of Burn Depth With Noncontact Ultrasonography," J. Burn Care Rehabil., 21:333-338 (2000).
Ennis W. J. et al. Ultrasound Therapy for Recalcitrant Diabetic Foot Ulcers, Results of a Randomized, Double-Bind, Controlled, MultiCenter Study; Ostomy Wound Management 2005; 51(8): pp. 24-39.
Department of Health & Human Services Letter dated Jun. 25, 2004 (3 pages).
Department of Health & Human Services Letter Dated May 17, 2005 (3 pages).
Image File Wrapper for U.S. Appl. No. 09/669,312, filed Jan. 12, 2001.
Image File Wrapper for U.S. Appl. No. 09/684,044, filed Oct. 6, 2002.
Image File Wrapper for U.S. Appl. No. 09/774,145, filed Jan. 30, 2001.
Image File Wrapper for U.S. Appl. No. 10/815,384, filed Apr. 1, 2004.
Image File Wrapper for U.S. Appl. No. 11/168,620, filed Jun. 27, 2005.
Image File Wrapper for U.S. Appl. No. 11/207,334, filed Aug. 18, 2005.
Image File Wrapper for U.S. Appl. No. 11/232,801, filed Sep. 22, 2005.
Image File Wrapper for U.S. Appl. No. 11/473,934, filed Jun. 23, 2006.
Image File Wrapper for U.S. Appl. No. 12/004,636, filed Dec. 21, 2007.
Image File Wrapper for U.S. Appl. No. 12/006,739, filed Jan. 4, 2008.
Image File Wrapper for U.S. Appl. No. 12/218,760, filed Jul. 17, 2008.
Design and Application of Low-Frequency Ultrasound and Its Combination With Laser Radiation in Surgery and Therapy—Critical Reviews in Biomedical Engineering; 2001; pp. 502-519.
European Search Report corresponding to EPO Appln. No. 01973544.8-2107-US0130096, Applicant Advanced Medical Applications Inc., dated Sep. 13, 2004.
International Search Report for PCT/US04/010448, Application Advanced Medical Applications Inc., dated Oct. 1, 2004.
Bisno, A.L., et al., "Murine Model of Recurrent Group G Streptococcal Cellulitis: No Evidence of Proective Immunity," Infection and Immunity, 65(12): 4926-4930 (1997).
Brooks, R.R., et al., "Canine Carrageenin-Induced Actue Paw Inflammation Model and its Response to Nonsteroidal Antiinflammatory Drugs," J. Parmacol Methods, 25: 275-283 (1991).
Chen, L., et al., The Disease Progression in the Keratin 14 IL-4-transgenic Mouse Model of Atopic Dermatitis Parallels the Up-regulation of B Cell Activation Molecules, Proliferation and Surface and Serum IgE, Clin, Exp. Immunolo, 142: 21-30 (2005).
Dong, C., et al., "MAP Kinases in the Immune Response," Annu. Rev. Immunol., 20: 55-72 (2002).
Hammer, R.E., et al., "Spontaneous Inflammatory Disease in Transgenic Rats Expressing HLA-B27 and Himan $\beta^2$m: An Animal Model of HLA-B27-Associated Human Disorders," Cell, 63: 1099-1112 (1990).
Haqqi, T.M., et al., "Restricted Heterogeneity in T-cell Antigen Receptor V$\beta$ Gene Usage in the Lymph Nodes and Arthritic Joints of Mice," PNAS, 89: 1253-1255 (1992).
Hurvitz, A.I., "Animal Model of Human Disease, Pemphigus Vulgaris, Animal Model: Canine Pemphigus Vulgaris," American Journal of Pathology, 98(3): 861-864 (1980).
Joe, B., et al., "Animal Models of Rheumatoid Arthitis," Molecular Medicine Today, 5: 367-369 (1999).
Keffer, J., et al., "Transgenic Mice Expressing Human Tumour Necrosis Factor: A Predictive Genetic Model of Arthritis," EMBO Journal, 10(13): 4025-4031 (1991).
Nishimuta, K., et al., "Effects of Metronidazole and Tinidazole Ointments on Models for Inflammatory Dermatitis in Mice," Arch. Dermatol. Res., 294: 544-551 (2003).
Liu, Z., et al., "Immunopathological Mechanism of Acantholysis in Pemphigus Vulgaris: An Explanation by Ultrastructural Observations," Society for Investigative Dermatology, DOI: 10.1111/j.0022-202X.2004.22438.x (2004).
Pelletier, J.P., et al., "In vivo Suppression of Early Experimental Osteoarthritis by Interleukin-1 Receptor Antagonist Using Gene Therapy," Arthritis Rheum., 40(6): 1012-1019 (1997).

Schon, M.P., "Animal Models of Psoriasis—What Can We Learn from Them?," J. Invest. Dermatol., 112(4): 405-410 (1999).
Trentham, D.E., et al., Autoimmunity to Type II Collagen: An Experimental Medicine, 146: 857-868 (1977).
Wooley, P.H., et al., "Type II Collagen-Induced Arthritis in Mice, I. Major Histocompatibility Complex (I Region) Linkage and Antibody Correlatesm," J. Exp. Med., 154: 688-700 (1981).
Yamamoto, T., "Characteristics of Animal Models for Scieroderma," Current Rheumatoloty Review, 1: 101-109 (2005).
Application and File History of U.S. Re-examination U.S. Appl. No. 90/007,613, now Ex Parte Reexamination Certificate No. 6,569,099 Cl, Inventor Babaev, filed Jul. 5, 2005.
Japanese Patent Application No. 2002-528187, dated Sep. 25, 2001, Applicant Babaev, Office Action dated Aug. 5, 2010, 5 pages.
Asakawa, M., et al., "WBN/Kob-Ht Rats Spontaneously Develop Dermatitis Under Conventional Conditions: Another Possible Model for Atopic Dermatitis," Ex. Anim., 54(5): 461-465 (2005).
Application and File History of U.S. Appl. No. 09/774,145, now U.S. Patent No. 6,960,173, Inventor Babaev, filed Jan. 30, 2001.
Application and File History of U.S. Appl. No. 11/168,620, now U.S. Patent No. 7,713,218, Inventor Babaev et al., filed Jun. 27, 2005.
Application and File History of U.S. Appl. No. 11/473,934, now U.S. Patent No. 7,785,277, Inventor Babaev et al., filed Jun. 23, 2006.
Application and File History of U.S. Appl. No. 12/004,636, Inventor Millerd et al., filed Dec. 21, 2007.
Clark (1996), The Molecular and Cellular Biology of Wound Repair, New York, NY, Plenum, pp. 3-50.
Janeway and Medzhitov (2002), Annual Review of Immunology 20: 197-216.
Office Action mailed Apr. 24, 2007, for Japanese App. No. 2002-560715 now JP-4,164,582.
European Supplementary Search Report corresponding to EP App. No. 02709235, dated Apr. 4, 2006.
International Search Report for PCT/US02/02724, Application Advanced Medical Applications Inc., dated Dec. 11, 2002.
Office Action, dated Nov. 2, 2009, for Canadian App. 2,521,117.
Office Action, dated Sep. 26, 2007, for Canadian App. 2,521,117.
Office Action, dated Aug. 5, 2009, for Canadian App. 2,421,798.
Office Action, dated Aug. 14, 2007, for Canadian App. 2,421,798.
Office Action, dated May 18, 2006, for Canadian App. 2,421,798.
Office Action, dated Jan. 18, 2008, for Chinese App. 01816263.0.
Office Action, dated Apr. 20, 2007, for Chinese App. 01816263.0.
Office Action, dated Nov. 5, 2009, for Japanese App. 2006-509708.
Office Action and Machine Translation Summary of Office Action, dated Jul. 7, 2008, for Mexican App. PA/a/2003/002535.
Office Action and Machine Translation Summary of Office Action, dated Apr. 25, 2006, for Mexican App. PA/a/2003/002535.
International Search Report for PCT/US01/30096, dated Sep. 25, 2002.
European Supplementary Search Report corresponding to EP App. No. 01973544, dated Sep. 1, 2004.
International Search Report for PCT/US2004/010448, dated Nov. 10, 2004.
Examination Report, dated Dec. 5, 2007, for Indian App. 1078/MUMNP/2005.
International Search Report for PCT/US01/31226, dated Sep. 11, 2002.
International Search Report for PCT/US02/02724, dated Dec. 11, 2002.
Examination Report, dated Jul. 1, 2008, for European App. 02709235.2-2305.
Examination Report, dated Nov. 21, 2007, for European App. 02709235.2-2305.
European Search Report for European App. 02709235.2-2305., dated Apr. 18, 2006.
Office Action, dated Jan. 14, 2010, for Canadian App. 2,436,812.
Office Action, dated May 3, 2006, for Canadian App. 2,436,812.
European Search Report for European App. 02709235, dated Apr. 4, 2006.
International Search Report for PCT/US06/24833, dated Feb. 22, 2007.
Written Opinion for International Application No. PCT/US06/24833, dated Feb. 22, 2007.

Japanese Office Action, dated Jul. 29, 2010 for Japanese Application No. 2002-528187.
International Search Report for PCT/US95/14926, dated Feb. 27, 1996.
Japanese Office Action, dated Dec. 18, 2009 for Japanese Application No. 2002-528187.
International Search Report for PCT/US2008/000151, dated Apr. 21, 2008.
Chinese Office Action, dated May 22, 2009 for Chinese Application No. 2006-800227860.
International Search Report for PCT/US2007/026251, dated May 7, 2008.
International Search Report for EP 04749758.1-2319, dated Mar. 30, 2011.
International Search Report for EP 04749758.1-2319, dated Apr. 30, 2010.
Office Action, dated Sep. 12, 2006, for Canadian App. 2,463,600.
European Examination Report for Application No. 01 973 554.8, dated Feb. 9, 2010.
European Examination Report for Application No. 08 866 666.4, dated Mar. 22, 2011.
Application and File History of U.S. Appl. No. 90/007,613, now Ex Parte Reexamination Certificate No. 6,569,099 C1, Inventor Babaev, filed Jul. 5, 2005.
Application and File History of U.S. Appl. No. 09/669,312, Inventor Babaev, filed Sep. 25, 2000.
Application and File History of U.S. Appl. No. 09/684,044, Inventor Babaev, filed Oct. 6, 2000.
Application and File History of U.S. Appl. No. 09/774,145, Inventor Babaev, filed Jan. 30, 2001.
Application and File History of U.S. Appl. No. 10/815,384, Inventor Babaev, filed Apr. 1, 2004.
Application and File History of U.S. Appl. No. 11/168,620, Inventor Babaev et al., filed Jun. 27, 2005.
Application and File History of U.S. Appl. No. 11/207,334, Inventor Babaev, filed Aug. 18, 2005.
Application and File History of U.S. Appl. No. 11/232,801, Inventor Babaev, filed Sep. 22, 2005.
Application and File History of U.S. Appl. No. 11/473,934, Inventor Babaev et al., filed Jun. 23, 2006.
Application and File History of U.S. Appl. No. 12/004,636, Inventor Millerd et al. filed Dec. 21, 2007.
Application and File History of U.S. Appl. No. 12/006,739, Inventor Peterson et al., filed Jan. 4, 2008.
Application and File History of U.S. Appl. No. 12/218,760, Inventor Peterson et al., filed Jul. 17, 2008.
Office Action from U.S. Appl. No. 12/317,588 dated Jul. 27, 2011.
Office Action from U.S. Appl. No. 12/317,710 dated Aug. 1, 2011.
Japanese Notification of Reasons for Rejection from Japanese Application No. 2008-518449 dated Jul. 29, 2011.
Application and File History of U.S. Appl. No. 12/507,289, filed Jul. 22, 2009, inventor Peterson.
Application and File History of U.S. Appl. No. 13/073,863, Inventor Babaev et al., filed Mar. 28, 2011.
Application and File History for U.S. Appl. No. 12/317,710, Inventor Peterson, filed Dec. 23, 2008.
Zharov et al., "Comparison possibilities of ultrasound and its combination with laser in surgery and therapy". pp. 331-339. In Biomedical Optoacoustics. 2000.
Application and File History for U.S. Appl. No. 12/317,588 filed Dec. 23, 2008, inventor Peterson.
European Office Action from European Application No. EP01973544.8 dated Dec. 16, 2011.

* cited by examiner

ULTRASONIC METHOD AND DEVICE FOR WOUND TREATMENT

This application is a Continuation-In-Part of U.S. application Ser. No. 09/669,312 filed on Sep. 25, 2000, by Eilaz Babaev, entitled: ULTRASONIC METHOD AND DEVICE FOR WOUND TREATMENT, the entire contents of which are hereby incorporated by reference.

FIELD OF THE INVENTION

The present invention relates to methods of using ultrasonic waves in wound treatment. More particularly, the present invention relates to a method of spraying a wound surface using ultrasonic waves for delivering drugs, killing bacteria, cleansing a surface and stimulating healthy tissue cells.

BACKGROUND OF THE INVENTION

Ultrasonic waves have been widely used in medical applications, including both diagnostics and therapy as well as many industrial applications. One diagnostic use of ultrasound waves includes using ultrasonic waves to detect underlying structures in an object or a human tissue. In this procedure, an ultrasonic transducer is placed in contact with the object or tissue via a coupling medium and high frequency (1-10 MHz) ultrasonic waves are directed into the tissue. Upon contact with various underlying structures, the waves are reflected back to a receiver adjacent the transducer. By comparison of the signals of the ultrasonic wave as sent with the reflected ultrasonic wave as received, an image of the underlying structure can be produced. This technique is particularly useful for identifying boundaries between components of tissue and can be used to detect irregular masses, tumors, and the like.

Two therapeutic medical uses of ultrasound waves include aerosol mist production and contact physiotherapy. Aerosol mist production makes use of a nebulizer or inhaler to produce an aerosol mist for creating a humid environment and delivering drugs to the lungs. Ultrasonic nebulizers operate by the passage of ultrasound waves of sufficient intensity through a liquid, the waves being directed at an air-liquid interface of the liquid at a point underneath or within the liquid. Liquid particles are ejected from the surface of the liquid into the surrounding air following the disintegration of capillary waves produced by the ultrasound energy. This technique can produce a very fine dense fog or mist. Aerosol mists produced by ultrasound are preferred over aerosol mists produced by other methods because a smaller particle size of aerosol can be obtained with the ultrasonic waves. One of the major shortcoming of inhalers and nebulizers is that the aerosol mist cannot be directed to a target area without an air stream, which decreases the efficiency of ultrasound. Ultrasonic sprayers such as those sold by Sonic and Materials Inc., Misonix Inc., Sono-Tek Inc. (see, for example, U.S. Pat. Nos. 4,153,201, 4,655,393, and 5,516,043) operate by passing liquid through a central orifice of an ultrasound instrument-tip. Major disadvantages of these sprayers include non-uniform particle size, heating of liquid flow, and less efficiency of ultrasound waves because of demolished end (radiation) surface configuration of the tip.

Contact physiotherapy applies ultrasonic waves directly to tissue in an attempt to produce a physical change in the tissue. In conventional ultrasound physiotherapy, an ultrasonic wave contacts the tissue via a coupling medium. Ultrasonic waves produced by the transducer travel through the coupling medium and into the tissue. The coupling medium is typically a bath of liquid, a jelly applied to the surface to be treated, or a water-filled balloon. Conventional techniques provide ultrasonic waves having an intensity of about 0.25 w/cm$^2$ to 3 w/cm$^2$ at a frequency of about 0.8 to 3 Megahertz. The treatment is applied to a skin surface for from about 1 to 30 minutes, two or three times a week. The coupling medium can provide a cooling effect which dissipates some of the energy produced by the ultrasonic transducer.

More importantly, a coupling medium or direct contact between the tissue and ultrasonic transducer is necessary to transmit the ultrasonic waves to the skin surface because ambient air is a relatively poor medium for the propagation of ultrasonic waves.

Several beneficial effects have been reported from contact ultrasound physiotherapy, such as, for example, the following: local improvement of the blood circulation, heating of the tissue, accelerated enzyme activity, muscle relaxation, pain reduction, and enhancement of natural healing processes. Despite these beneficial effects, current techniques of medical physiotherapy using ultrasonic waves are limited by the necessity of providing a direct contact interface between the ultrasonic transducer and the tissue to maintain an effective transmission of the ultrasonic waves from the transducer to the tissue.

The necessity of direct contact with or without a coupling medium makes current methods undesirable. Some tissue conditions may be accessible to contact ultrasound devices but would be impractical for contact ultrasound treatment. For example, fresh or open wounds resulting from trauma, burns or surgical interventions are not suitable for direct contact ultrasound treatment because of the structural nature of the open wound and the painful condition associated with those wounds. Moreover, conventional contact ultrasound may have a destructive effect on these types of open wounds due to the close proximity of an oscillating tip of an ultrasonic transducer relative to the already damaged tissue surface.

OBJECT OF THE INVENTION

It is an object of the invention to provide an improved method and device for treating wounds.

It is also an object of this invention to provide a method and device for treating wounds using ultrasonic waves.

It is a further object of the invention to provide a method and device for delivering drugs, killing bacteria, cleansing a surface, or stimulating healthy tissue cell growth.

It is a yet further object of the invention to treat a wound by spraying the surface of the wound with aerosol mist produced by ultrasonic waves.

These and other objects of the invention will become more apparent from the discussion below.

SUMMARY OF THE INVENTION

The present invention provides an apparatus and method for generating ultrasonic energy from a non-contact distance from the surface of the wound; and delivering the generated ultrasonic energy to the wound through a gaseous medium ("dry" approach), wherein the generated ultrasonic energy has an intensity capable of penetrating the wound tissue to a beneficial depth to provide a therapeutic effect for decreasing the healing time for the wound.

The present invention further relates to a method and device for spraying ("wet" approach) a wound surface to deliver drugs, kill bacteria, or cleanse a surface by non-contact application of an ultrasound transducer tip. The method applies ultrasonic waves to the wound without requiring direct or indirect (via a traditional coupling medium) contact between the ultrasonic wave transducer and the wound to be sprayed.

The method of the invention comprises producing a directed spray of liquid or powder particles produced by contact of the liquid or powder with a free end surface of an ultrasonic transducer. The ultrasonic waves cause the spray to project outwardly from the distal end surface of the ultrasonic transducer, and the particle spray is directed onto the wound. The particles of the spray provide a medium for propagation of the ultrasonic waves emanating from the distal end surface. According to the method of the present invention a directed particle spray created by low frequency ultrasound waves onto a wound, delivers drug, kills bacteria on the wound, increases blood flow, and removes dirt and other contaminants from the wound's surface (mechanical cleansing).

This method of drug delivery is particularly advantageous on tissues for which local topical application of a drug is desirable but contact with the tissue is to be avoided. Furthermore, the low frequency ultrasound waves used in the method energize the drug and cause penetration of the drug below the surface of the tissue. Finally, the bacteria killing method is effective when applied to the surface whether the liquid or powder sprayed is a drug (an antiseptic or antibiotic), oil, saline, distilled water, etc.

DETAILED DESCRIPTION OF THE INVENTION

The device of the invention that produces a spray is characterized by means for first delivering the liquid to a lateral surface of an ultrasonic transducer tip adjacent to a free end surface such that the liquid is pulled to the free end surface by a vacuum (negative pressure) created by the ultrasound waves on the free end surface of the transducer tip. This effect can be achieved while the angle between the ultrasound instrument and the horizontal is modified up to 90°. (This acoustical effect of delivering liquid from radial side of a tip to the free end was discovered by the inventor of this invention and is called the "Babaev effect".) This effect occurs when liquid is delivered to the radial surface of a transducer tip from 360° by perimeter as a top, side, bottom, etc.

For the above purpose the device must have a so-called nozzle from steel (nondisposable) or plastic (disposable) with a different design of valve. The nozzle allows delivery of liquid to the lateral surface of the transducer tip or directly to the distal side (radiation surface) of the ultrasound transducer to act as a sprayer or atomizer.

One of the major advantages of the invention is the uniformity of the spray particles generated. Because liquid or powder is sprayed from a solid radiation surface, there is substantial uniformity of particle size, about 90% or greater, preferably from about 90 to 96%. It is provided that the distal radiation surface is driven with constant frequency to create the spray. It is also provided that the frequency can be modulated during treatment and that the distal radiation surface is driven with a sinusoidal, rectangular, trapezoidal or triangular wave form.

The step of producing the spray can further include operating the transducer to produce ultrasonic waves having a frequency of from about 18 kHz to 10,000 MHz. Frequencies below 18 kHz, i.e., from about 1 to 18 kHz, can be used as well; however, this lower range is less desirable because this range of sound wave can be uncomfortable to the patient and operator (without ear protection or the like). Frequencies in the range of from about 30 to 100 kHz are preferred, and frequencies of about 40 kHz are most preferred.

The separation distance between the free end surface of the transducer and the surface or object to be sprayed should be a "non-contact" distance of at least 0.1 in. (2.5 mm). Preferably the separation distance is from about 0.1 in. (2.5 mm) to 20 in. (51 cm), more preferably from about 0.1 in. (2.5 mm) to 5 in. (12.7 cm). The liquid or powder to be sprayed can be any appropriate carrier such as water (regular or distilled), saline solution, or oil to be applied to tissue, such as a vegetable, peanut, or canola oil, optionally with a soluble pharmaceutical (e.g., an antibiotic), antiseptic, conditioner, surfactant, emollient, or other active ingredient. The pharmaceutical or the like is preferably present in a concentration sufficiently low to be soluble but high enough to be effective for the intended purpose.

It is within the scope of the invention that the liquid to be sprayed could comprise a mixture of two or more immiscible liquids or a heterogeneous mixture of a solution and small particles. It is also within the scope of the invention that the spray could comprise particles, such as powder.

The spray produced according to the invention is directed to the object, surface, or tissue to be sprayed for the time and frequency required to accomplish a particular purpose or treatment. It is believed that a minimum length of spray of at least one second will be required; however, the length or duration of the spray could be from about one second to as much as a minute or more, even 30 minutes. Numerous factors or circumstances, such as, for example, the area to be sprayed (e.g., the size of a wound), the volume rate of spray produced, the concentration of active ingredient, etc., will impact upon the duration and/or frequency of the spraying. Spraying could be required from one or more times daily to as little as two or three times a week or month.

According to the invention ultrasonic waves are applied to a wound without establishing contact, directly or indirectly, between the ultrasonic transducer and the wound. For example, surfaces of the human body especially suited for treatment with the method of the present invention include infected and inflammatory situations in open wounds, including trauma or gun shut wounds, fire and chemical burns.

In addition, the method of the present invention is particularly suited to directing a spray into orifices or other body crevices that are difficult to access.

Wound treatment according to the invention has several advantages. First, this method topically applies medicines such as liquid antibiotics to the wound surface without the need to contact infected, inflamed or painful tissue with an instrument. And second, a significant bactericidal effect occurs when a wound surface is sprayed using the method of the present invention.

Moreover, aside from the bactericidal effect and advantages of non-contact treatment, using the method of the present invention gave a significant reduction in volume used of liquid medicine used as compared with traditional methods for wound treatment. Similarly, this allows for precise dosage of the sprayed liquid to permit a user, such as a physician, to administer the desired volume of liquid at a desired rate and duration.

It has been found that the method of the present invention decreases healing times for inflammatory and purulent infected wounds that is from about 1.5 to 3 times faster than traditional methods. This effect results from a bactericidal, blood flow increasing and mechanical cleansing effect of the atomized spray particles, which have ultrasound energy due to the ultrasonic waves. The spray mechanically scrubs the surface of tissue to remove dirt, dead tissue, and purulent buildup on the tissue surface. The mentioned healing effect also results of energized and highly activated antibiotics, drug penetration into the tissue surface up to 0.5 mm in depth under influence of ultrasound waves.

Additionally, a combination of the low frequency ultrasonic waves and the sonicated medicines (highly activated by ultrasonic energy) destroy the surface bacteria to result in a higher disinfecting property of sonicated liquids as compared to ordinarily applied liquids.

The spray of the present method also stimulates healthy cell growth to aid in granulization and epithelization of the healing tissue.

Other applications of the invention can be directed to non-medical uses such as cleansing, sterilizing and coating surfaces of objects and food.

The method of the present invention offers an approach that may re-establish use of some traditional antibiotics and establish a method fighting bacteria without antibiotics when necessary. The effect of the method of the present invention in highly activating antibiotics may allow some traditional antibiotics to overcome bacteria which have become resistant to that antibiotic. Moreover, independent of the sonication effect of the antibiotics, the low frequency ultrasonic waves applied in the method of the present invention physically destroy bacteria. The combination of the highly activated antibiotics and of the low frequency ultrasonic waves in the method of the present invention produce a strong bactericidal effect not found in mere topical application or oral ingestion of antibiotics. This combined effect has been shown to significantly increase the healing of purulent infected wounds.

The present method also provides a system of non-contact drug delivery without use of a compression sprayer system. This simplifies the design of a non-contact drug delivery sprayer and reduces the weight of the sprayer. More importantly, not using compression to propel the atomized particles preserves the ultrasound energy carried by the spray particles.

Delivery of ultrasound energy in accordance with the present invention has been proven to destroy bacteria by action of the ultrasonic waves and by highly activated liquid medicines applied to the tissue.

The method of the present invention provides a method of compressionless no contact drug delivery.

Figure 1:
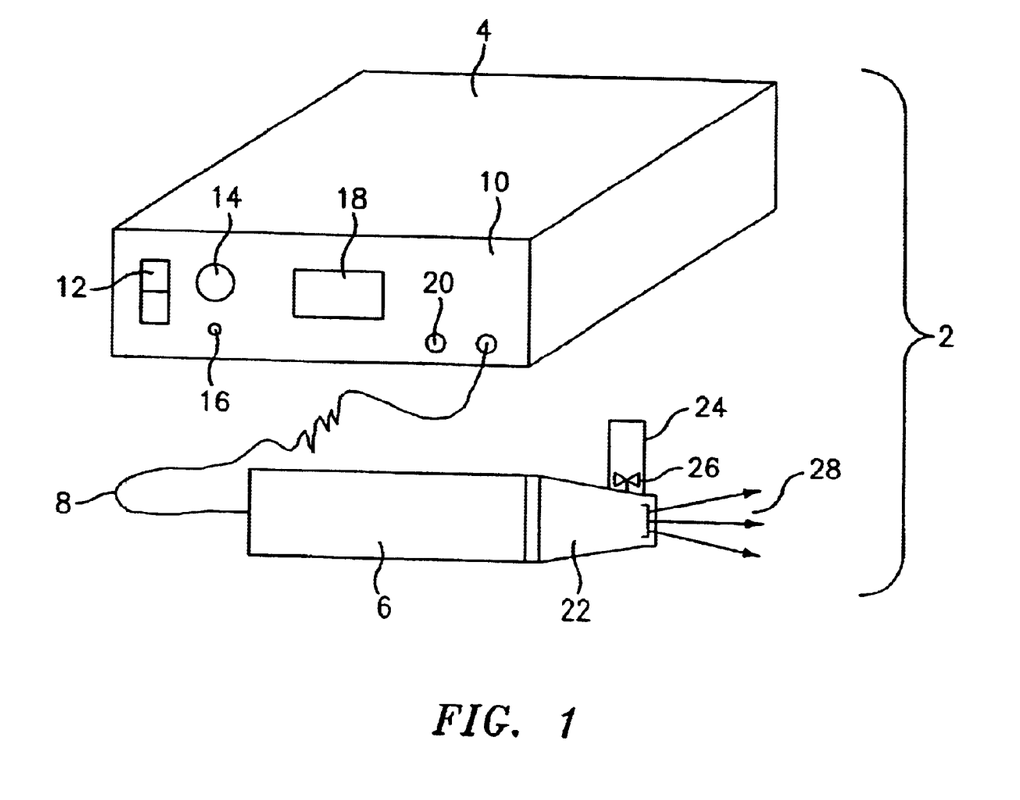
FIG. 1 is a perspective view of an ultrasonic wound treatment system according to the present invention.

The invention is better appreciated by making reference to the drawings. In FIG. 1, an ultrasonic treatment system 2 comprises an ultrasound wave generator 4, connected to an ultrasound transducer 6 by a cable 8. The wave generator 4, which is conventional, may have a front panel 10 with a power button 12, a timer 14, a control button 16, a display 18, and one or more jacks 20, for example, for connecting a footswitch. A nozzle 22 having a liquid reservoir 24 with a valve 26 is attached to the distal portion of transducer 6. Arrows 28 represent the direction of the spray produced.

Figure 2:
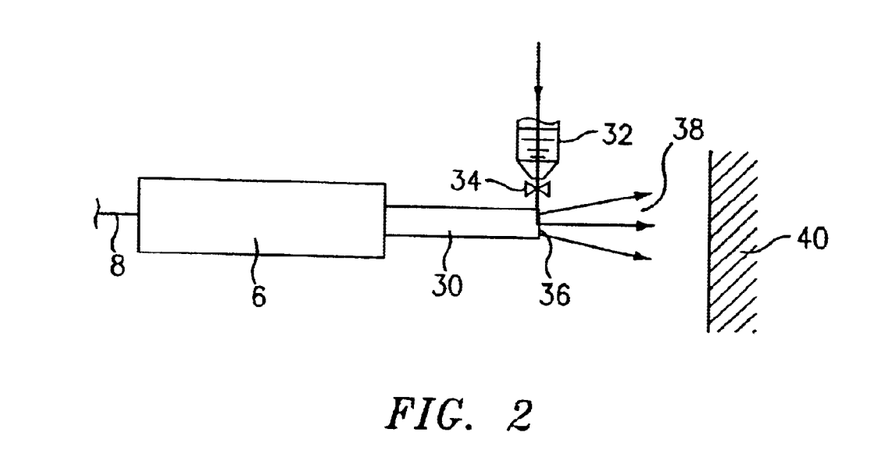
FIG. 2 is a lateral schematic view of an ultrasonic sprayer according to the Present invention.

FIG. 2 is a simplified representation of an ultrasonic device and spray according to the invention. Transducer 6 has a distal transducer tip or horn 30. Liquid from a liquid reservoir 32 flows through a valve 34 to a position adjacent the distal radiation surface 36 of a horn 30. Transducer 6 is attached to an ultrasound source via cable 8. A liquid mist is directed in the direction of arrows 38 to target tissue or surface 40 (wet approach).

Figure 3:
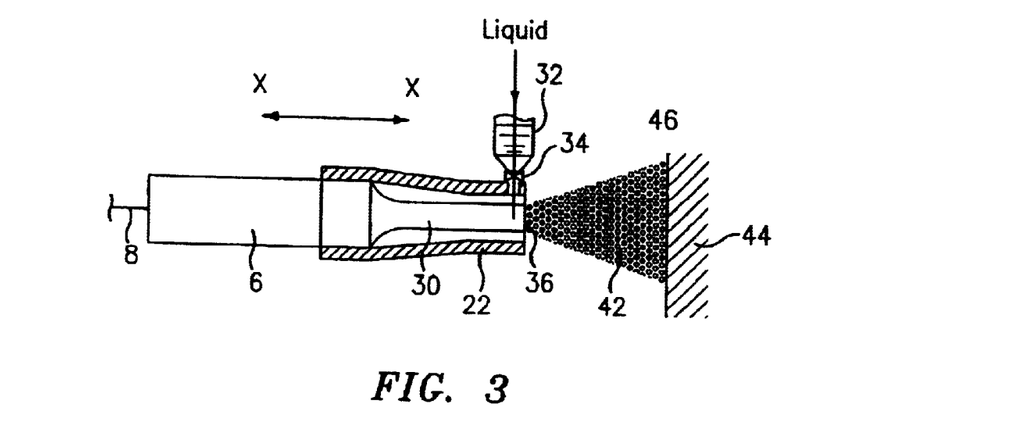
FIG. 3 is a partly cross-sectional view of an ultrasonic sprayer according to the present invention.

FIG. 3 is an enlarged, partly cross-sectional view of a section of FIG. 1 illustrating a spray created by the device according to the method of the present invention. This device is a modification and implementation of a device disclosed in U.S. Pat. No. 5,076,266, which is incorporated herein by reference. As can be seen in more detail in FIG. 3, nozzle 22 surrounds ultrasound horn 30. Also, liquid reservoir 32 has a valve 34 positioned between reservoir 32 and the distal surface 36 of ultrasonic horn 30. A conical spray pattern of liquid droplets 42 is directed at a surface or tissue 44 of a target. This configuration is effective to spray liquid onto a surface and to deliver ultrasonic waves to that surface, such as, for example, the surface of a wound.

Valve 34 allows liquid to flow to distal tip 36 as drops or as a continuous flow through gap 46. Valve 34 may be located anywhere, including between reservoir 32 and horn 30. Mechanical movement of the horn 30 in the direction x-x causes liquid to flow to the distal end or radiation surface 36.

Figure 4A:
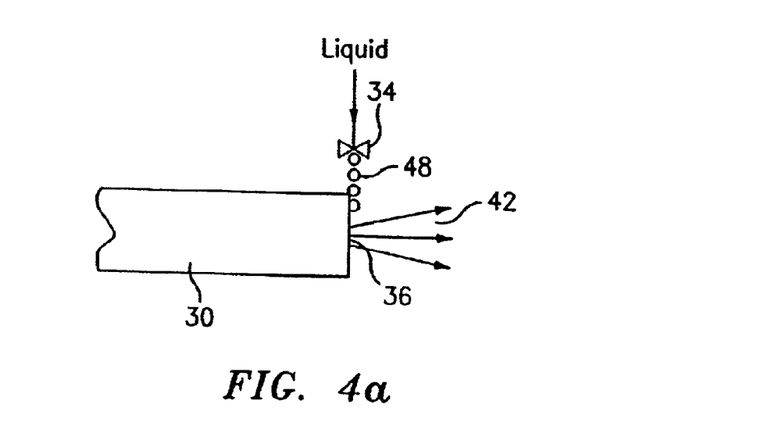
FIG. 4a is a detailed view of the sprayer, illustrated in FIG. 3 for spraying liquid from a radiation surface.

FIG. 4(a) is a view of the ultrasonic sprayer as used in a method of the present invention for spraying liquid 48 directed to distal end (radiation surface) 36.

Figure 4B:
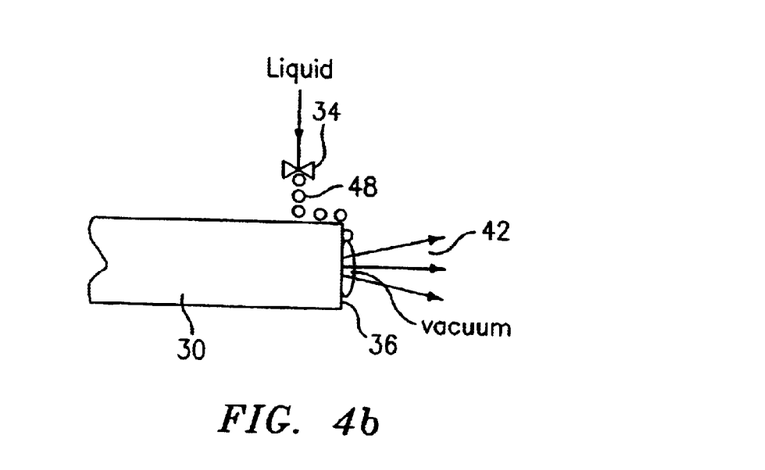
FIG. 4b is a detailed view of the sprayer illustrated in FIG. 3 for spraying liquid from a side (radial) surface.

FIG. 4(b) is a view of the basic spraying method from side (radial) surface of the tip based on the Babaev effect. In this case liquid or drug directed to the radiation surface 36 of ultrasound horn 30 becomes sonicated (ultrasonically energized), after being pulled forward by negative pressure (vacuum) created by ultrasound waves and sprays.

Figure 5:
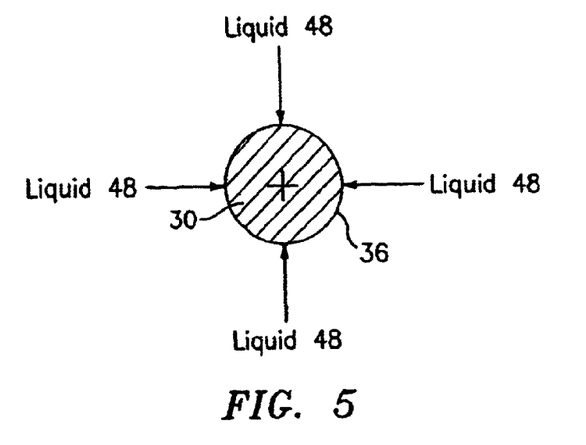
FIG. 5 is a cross-sectional front view of a distal end of an ultrasonic transducer when liquid is delivered to the side or radiation surface of the transducer tip from 360° along its perimeter.

As shown in FIG. 5, liquid is delivered to the side or radiation surface 36 of transducer horn 30 from 360° along its perimeter as a top, side, bottom, etc.

Figure 6:
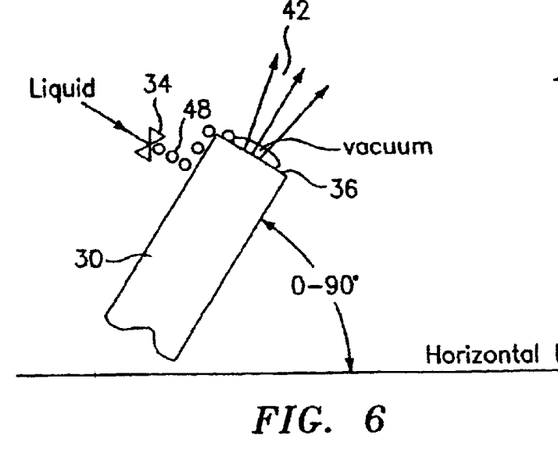
FIG. 6 is a variation of FIG. 4b illustrating the spraying effect by changing the angle between the ultrasound instrument and horizontal line from 0° to 90°.
Figure 7A:
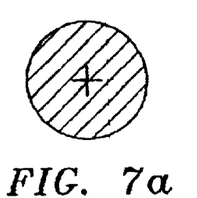
FIGS. 7a-7g are each a front cross-sectional view of an ultrasound tip configuration.
Figure 7B:
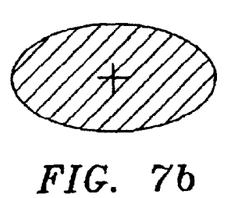
Figure 7C:
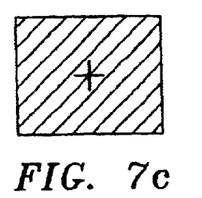
Figure 7D:
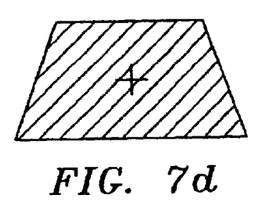
Figure 7E:
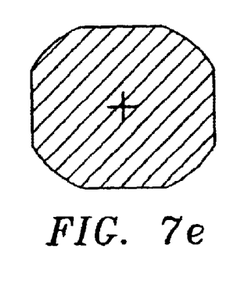
Figure 7F:
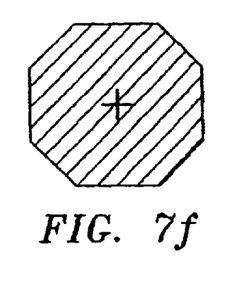
Figure 7G:
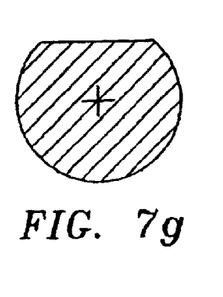

In the embodiment of the invention shown in FIG. 6, a partial section of transducer horn 30 is elevated from the horizontal up to 90°. Due to the Babaev effect, liquid 48 still travels to radiation surface 36.

Figure 8A:
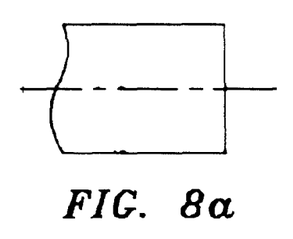
FIGS. 8a-8i are each an enlarged side view of a different modification of a tip end shape of the ultrasonic sprayer according to the present invention.
Figure 8B:
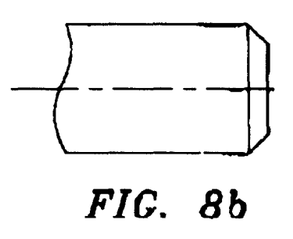
Figure 8C:
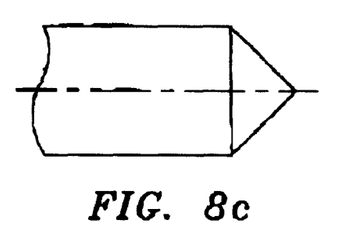
Figure 8D:
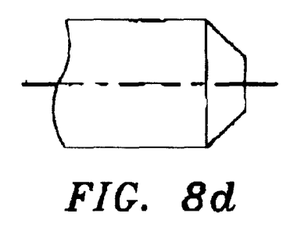
Figure 8E:
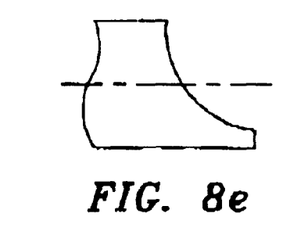
Figure 8F:
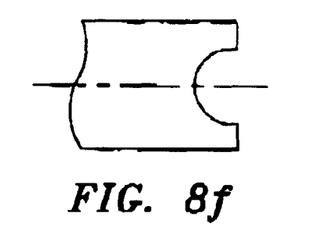
Figure 8G:
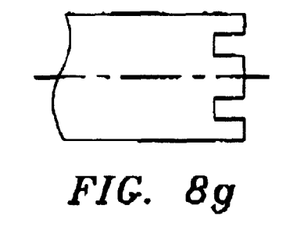
Figure 8H:
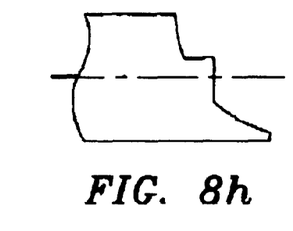
Figure 8I:
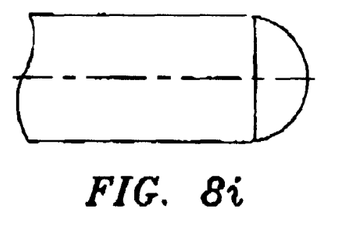

The ultrasound tip or horn may have a regular or irregular lateral cross-section, including circular, oval, elliptical, rectangular, trapezoidal, or a combination thereof. For example, FIGS. 7(a) to 7(g) are each a view of a cross-section of an ultrasound tip or horn. Also, the distal end shape of the ultrasound tip or horn longitudinal cross-section may vary and may be rectangular, elliptical, oval, spherical, conical, curved, stepped, with chamfer, etc. See, for example, FIGS. 8(a) to 8(n), which are each an enlarged view in section of a different modification of a tip of the sprayer as used in the method of the present invention. The preferred shape is rectangular, because of radiation beams from ultrasound tip surface fully directed to the target (wound). With the spherical, elliptic and oval (FIG. 8(e)) form of shape end, radiation beams are focused at a focal point. However, with other forms of shape end, radiation beams are spread, thus partially reaching the target.

Figure 9A:
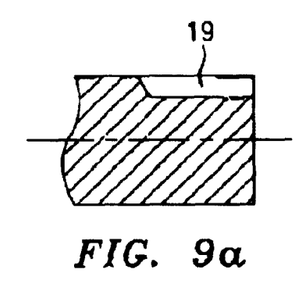
FIGS. 9a, 9b, and 9c represent cross-sectional, distal, and lateral views, respectively, of the top of an ultrasonic sprayer having a slot, groove, or thread.
Figure 9B:
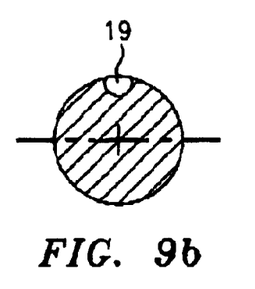
Figure 9C:
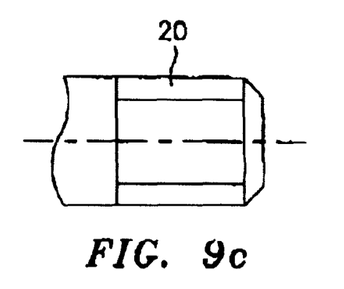
Figure 10:
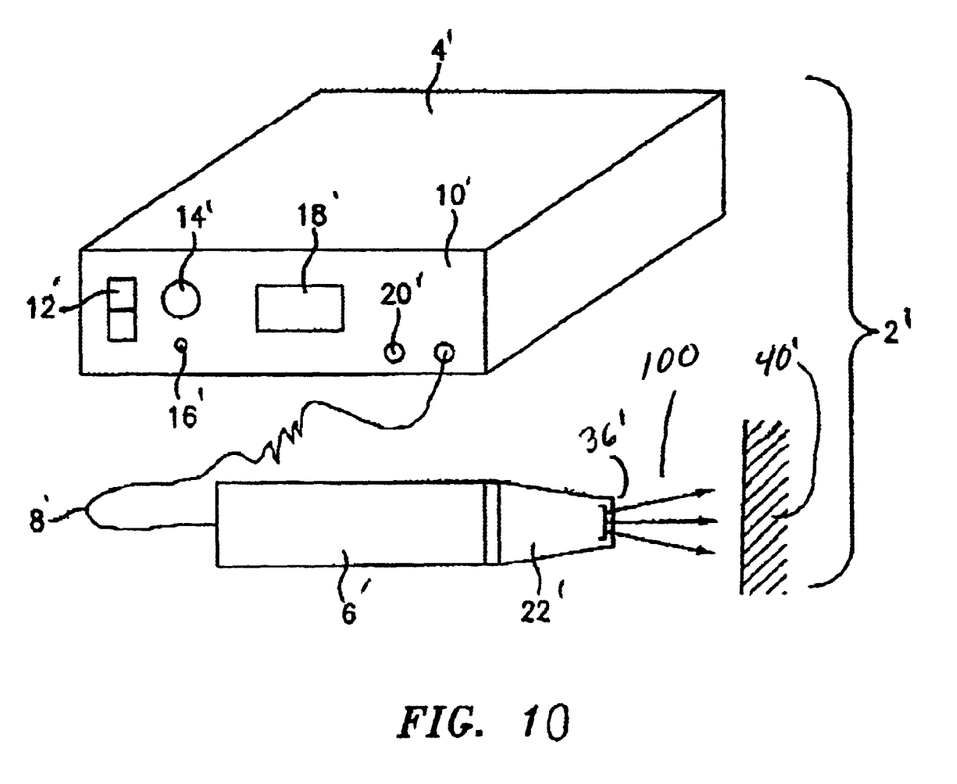
FIG. 10 is a schematic representation of a method of delivery of ultrasonic energy delivered through a gaseous medium, accordance with another embodiment of the present invention.
Figure 11:
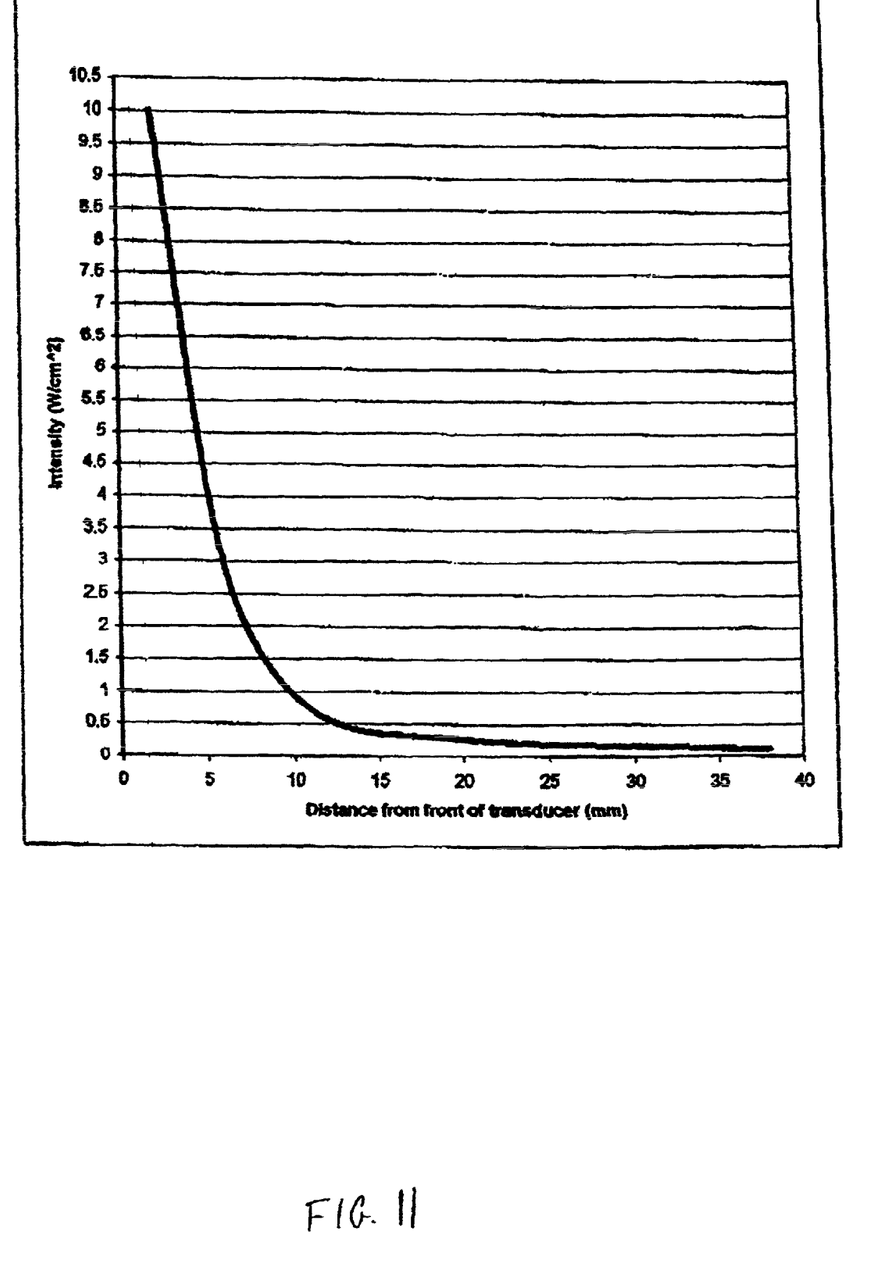
FIG. 11 is a plot of experimental results achieved upon delivering ultrasound energy substantially through a gaseous medium to a wound in accordance with the present invention.

Radial side surface of the distal end of the tip may have a slot (groove) or thread for liquid to be directed to the radiation surface (FIG. 9).

FIGS. 9a to 9c are each a view of a radial side surface of the distal end of the tip which has a slot (groove) 19 or thread 20 for liquid to be directed to the radiation surface.

In another embodiment, ultrasonic energy is delivered to the wound without the use of the spray, i.e., the ultrasonic energy is delivered through a medium other than a spray, including a gaseous medium, such as pure air, e.g., ambient air, where the ultrasound transducer 6 is positioned at a non-contact distance from the wound for providing a therapeutic and beneficial effect. The ultrasound waves, even without the use of a spray, destroy surface bacteria and stimulate health cell growth. This method of wound treatment is particularly advantageous on wounds for which contact with the wound should be avoided.

With reference to FIG. 10, an ultrasonic treatment system 2' is shown including an ultrasound wave generator 4' for generating ultrasound energy connected to an ultrasound transducer 6' by a cable 8'. Transducer 6' has a radiation surface 36' from which the ultrasound energy is emitted and directed to wound 40'. The wave generator 4', which is conventional, may have a front panel 10' with a power button 12', a timer 14', a control button 16', a display 18', and one or more jacks 20', for example, for connecting a footswitch. Arrows 100 represent the direction of ultrasound energy generated and directed toward wound 40'. Unlike the above embodiments, a liquid or powder is not contacted with the ultrasonic transducer for generating a spray and directing it to the wound 40'. The ultrasonic energy is delivered through a medium other than a spray, including a gaseous medium, such as pure air ("dry" approach).

In a preferred embodiment of the invention, wherein the ultrasonic energy is delivered to the wound 40' through a gaseous medium, such as pure air, for achieving a therapeutic effect at the wound 40', the frequency of the ultrasonic energy generated is selected to be a low frequency. By using a low frequency, a particular or predetermined amplitude for the generated ultrasonic energy is achieved, which is capable of being delivered to the wound with an intensity capable of providing a therapeutic effect to the wound 40'. Preferably, the amplitude achieved by the ultrasonic energy is at least 3 microns and preferably at least 10 micros. Preferably, the frequency used is in the range of 20 kHz-50 MHz, wherein a preferred range is 20-200 kHz, a more preferred range is 20-40 kHz and a most preferred value is 40 kHz, wherein most preferably the lower limit of the frequency used is outside of the human hearing range.

Furthermore, it is advantageous to use a radiation surface 36' having a shape and size selected to achieve delivery of the ultrasonic energy to the wound where the delivered ultrasonic energy has an intensity capable of providing a therapeutic effect to the wound. Selection of the shape and size of the radiation surface 36' in combination with selection of the frequency and amplitude of the ultrasonic energy used is advantageous in achieving delivery of the ultrasonic energy to the wound wherein the ultrasonic energy has an intensity capable of achieving a therapeutic effect to the wound. Preferably, the perimeter of the radiation surface 36' is round and has a relatively large diameter. Actual selection of the diameter is dependent upon the frequency and amplitude selected. Furthermore, the shape of the radiation surface 36' is selected from one of flat, concave, convex, and a combination thereof.

With respect to FIG. 11, results are shown of experimentation at Celleration Acoustic Laboratory, Eden Prairie, Minn. Ultrasonic energy having an intensity capable of providing a therapeutic effect was delivered through air (no spraying of liquid or powder) to a wound using an ultrasound transducer positioned at a non-contact distance from the surface of the wound, as shown by FIG. 10. The ultrasonic energy was generated at a frequency of 40 kHz and an amplitude of 61 microns. The transducer radiation surface was flat, rounded and had a diameter of 1 cm. Hydrophone model number PVDF-Z44-1000 and hydrophone amplifier model number A17db, both manufactured by ONDA Corporation, Sunnyvale, Calif., were employed, using an amplifier gain of 7.44. As shown, with the transducer positioned at a distance of between 2.5 mm and 38 mm from a wound, ultrasonic energy was delivered to the wound having an intensity capable of providing a therapeutic effect to the wound; the intensity being within the range of from 0.1 W/cm$^2$ to 10 W/cm$^2$.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A method for treating a wound comprising the steps of:

generating ultrasonic energy having a frequency in the range of about 20 kHz to less than 50 kHz; and delivering the generated ultrasonic energy to the wound through a gaseous medium from a non-contact distance from the surface of the wound in the absence of a coupling medium and without direct contact between an apparatus for generating and delivering ultrasonic energy and the wound and other patient tissue, wherein the generated ultrasonic energy has an intensity in the range of about 0.1 watts/cm$^2$ to about 3 watts/cm$^2$, and wherein the non-contact distance is at least 2.5 mm from the surface of the wound.

2. The method according to claim 1, wherein the generating step includes generating the ultrasonic energy with a particular amplitude indicative of an intensity capable of penetrating the wound to a beneficial depth to provide a therapeutic effect for decreasing the healing time for the wound.

3. The method according to claim 2, wherein the generating step further includes the step of generating the ultrasonic energy with a frequency capable of achieving the particular amplitude.

4. The method according to claim 3, wherein the frequency is in the range of about 20 kHz to about 40 kHz.

5. The method according to claim 2, wherein the particular amplitude is at least 3 microns.

6. The method according to claim 2, wherein the particular amplitude is at least 10 microns.

7. The method according to claim 2, wherein the particular amplitude is at least 35 microns.

8. The method according to claim 7, wherein the particular amplitude is at least 61 microns.

9. The method according to claim 1, further comprising the step of providing a transducer for delivering the ultrasonic energy, said transducer having a radiation surface with a surface area dimensioned for achieving delivery of the ultrasonic energy to the wound with an intensity capable of achieving a therapeutic effect.

10. The method according to claim 9, wherein the radiation surface is positioned from about 2.5 mm to about 51 cm from the surface of the wound.

11. The method according to claim 1, further comprising the step of providing a transducer for delivering the ultrasonic energy, said transducer having a radiation surface with a rounded perimeter for achieving delivery of the ultrasonic energy to the wound with an intensity capable of achieving a therapeutic effect.

12. The method according to claim 1, further comprising the steps of:
    providing a transducer for delivering the ultrasonic energy having a radiation surface; and
    selecting at least one of a size of a surface area of the radiation surface, a shape of a peripheral boundary of the radiation surface, a frequency of the generated ultrasonic energy, and an amplitude of the generated ultrasonic energy for achieving delivery of ultrasonic energy to the wound with an intensity capable of achieving a therapeutic effect.

13. The method of claim 1, further comprising the steps of:
    providing a transducer for delivering the ultrasonic energy having a radiation surface; and
    selecting a combination of a size of a surface area of the radiation surface, a shape of a peripheral boundary of the radiation surface, a shape of the curvature of the radiation surface selected from one of flat, concave, convex and a combination thereof, a frequency of the generated ultrasonic energy, and an amplitude of the generated ultrasonic energy for achieving a therapeutic effect.

14. The method according to claim 1, wherein the generating step includes the steps of generating the ultrasonic energy with a constant or modulated frequency having a wave form selected from the group consisting of sinusoidal, rectangular, trapezoidal, and triangular wave forms.

15. The method according to claim 1, wherein the method provides a therapeutic effect selected from the group consisting of increasing blood flow to the wound and stimulating cell growth.

16. The method according to claim 1, wherein the gaseous medium includes a substantial expanse of a substantially purely gaseous medium.

17. The method according to claim 1, wherein the non-contact distance is about 2.5 mm to 51 cm from the surface of the wound.

18. The method according to claim 1, wherein the frequency is in the range of from about 30 to less than 50 kHz.

19. The method according to claim 1, wherein the frequency is about 40 kHz.

20. The method according to claim 1, wherein the wound is an open wound.

21. A method for treating a wound comprising the steps of:
    generating ultrasonic energy having a particular amplitude and having a frequency in the range of about 20 kHz to less than 50 kHz; and
    delivering the generated ultrasonic energy to the wound through a gaseous medium from a non-contact distance from the surface of the wound and without direct contact between an apparatus for generating and delivering ultrasonic energy and the wound and other patient tissue, wherein the gaseous medium does not include a liquid spray or other coupling medium, wherein the generated ultrasonic energy has an intensity in the range of about 0.1 watts/cm$^2$ to about 3 watts/cm$^2$, wherein the particular amplitude is indicative of said intensity, and wherein the non-contact distance is at least 2.5 mm from the surface of the wound.

22. The method according to claim 21, wherein the wound is an open wound.

23. A method for treating a wound comprising the steps of:
    generating ultrasonic energy having a frequency in the range of about 20 kHz to less than 50 kHz; and
    delivering the generated ultrasonic energy to the wound through a gaseous medium from a non-contact distance from the surface of the wound and without direct contact between an apparatus for generating and delivering ultrasonic energy and the wound and other patient tissue, wherein the gaseous medium does not include a liquid spray or other coupling medium, wherein the generated ultrasonic energy has an intensity capable of penetrating the wound to a beneficial depth to provide a therapeutic effect for decreasing the healing time for the wound, wherein the frequency is capable of achieving a particular amplitude indicative of an intensity in the range of about 0.1 watts/cm$^2$ to about 3 watts/cm$^2$, and wherein the non-contact distance is at least 2.5 mm from the surface of the wound.

24. A method for treating a wound comprising the steps of:
    generating ultrasonic energy having an amplitude of at least 3 microns and having a frequency in the range of about 20 kHz to less than 50 kHz; and
    delivering the generated ultrasonic energy to the wound through a gaseous medium from a non-contact distance from the surface of the wound and without direct contact between an apparatus for generating and delivering ultrasonic energy and the wound and other patient tissue, wherein the gaseous medium does not include a liquid spray or other coupling medium, wherein the generated ultrasonic energy has an intensity in the range of about 0.1 watts/cm$^2$ to about 3 watts/cm$^2$, and wherein the non-contact distance is at least 2.5 mm from the surface of the wound.

25. The method according to claim 24, wherein the ultrasonic energy has an amplitude of at least 10 microns.

* * * * *